(12) United States Patent
Tsokos

(10) Patent No.: US 10,028,975 B2
(45) Date of Patent: Jul. 24, 2018

(54) METHODS FOR TREATING ISCHEMIA-REPERFUSION INJURY

(71) Applicant: Beth Israel Deaconess Medical Center, Inc., Boston, MA (US)

(72) Inventor: George C. Tsokos, Boston, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 14/656,558

(22) Filed: Mar. 12, 2015

(65) Prior Publication Data
US 2016/0199402 A1    Jul. 14, 2016

Related U.S. Application Data

(63) Continuation of application No. 13/277,046, filed on Oct. 19, 2011, now abandoned.

(60) Provisional application No. 61/394,560, filed on Oct. 19, 2010.

(51) Int. Cl.
| | | |
|---|---|---|
| *A61K 31/713* | (2006.01) | |
| *A61K 31/5383* | (2006.01) | |
| *A61K 31/675* | (2006.01) | |
| *A61K 45/06* | (2006.01) | |
| *G01N 33/573* | (2006.01) | |
| *C12N 15/113* | (2010.01) | |

(52) U.S. Cl.
CPC ........ *A61K 31/713* (2013.01); *A61K 31/5383* (2013.01); *A61K 31/675* (2013.01); *A61K 45/06* (2013.01); *G01N 33/573* (2013.01); *C12N 15/1137* (2013.01); *C12N 2310/14* (2013.01); *C12Y 207/10002* (2013.01); *G01N 2333/91205* (2013.01); *G01N 2500/04* (2013.01)

(58) Field of Classification Search
CPC .............. A61K 31/713; A61K 31/5383; A61K 31/675; A61K 45/06
See application file for complete search history.

(56) References Cited

U.S. PATENT DOCUMENTS 7,582,648 B2    9/2009    Singh et al.

*Primary Examiner* — Sahar Javanmard
(74) *Attorney, Agent, or Firm* — Clark & Elbing LLP

(57) ABSTRACT

The present invention features methods for treating, reducing the likelihood of, or attenuating an ischemia-reperfusion injury in a subject by administering an inhibitor of spleen tyrosine kinase (Syk). Also included in the present invention are methods for identifying compounds that inhibit Syk for the treatment of an ischemia-reperfusion injury.

14 Claims, 9 Drawing Sheets

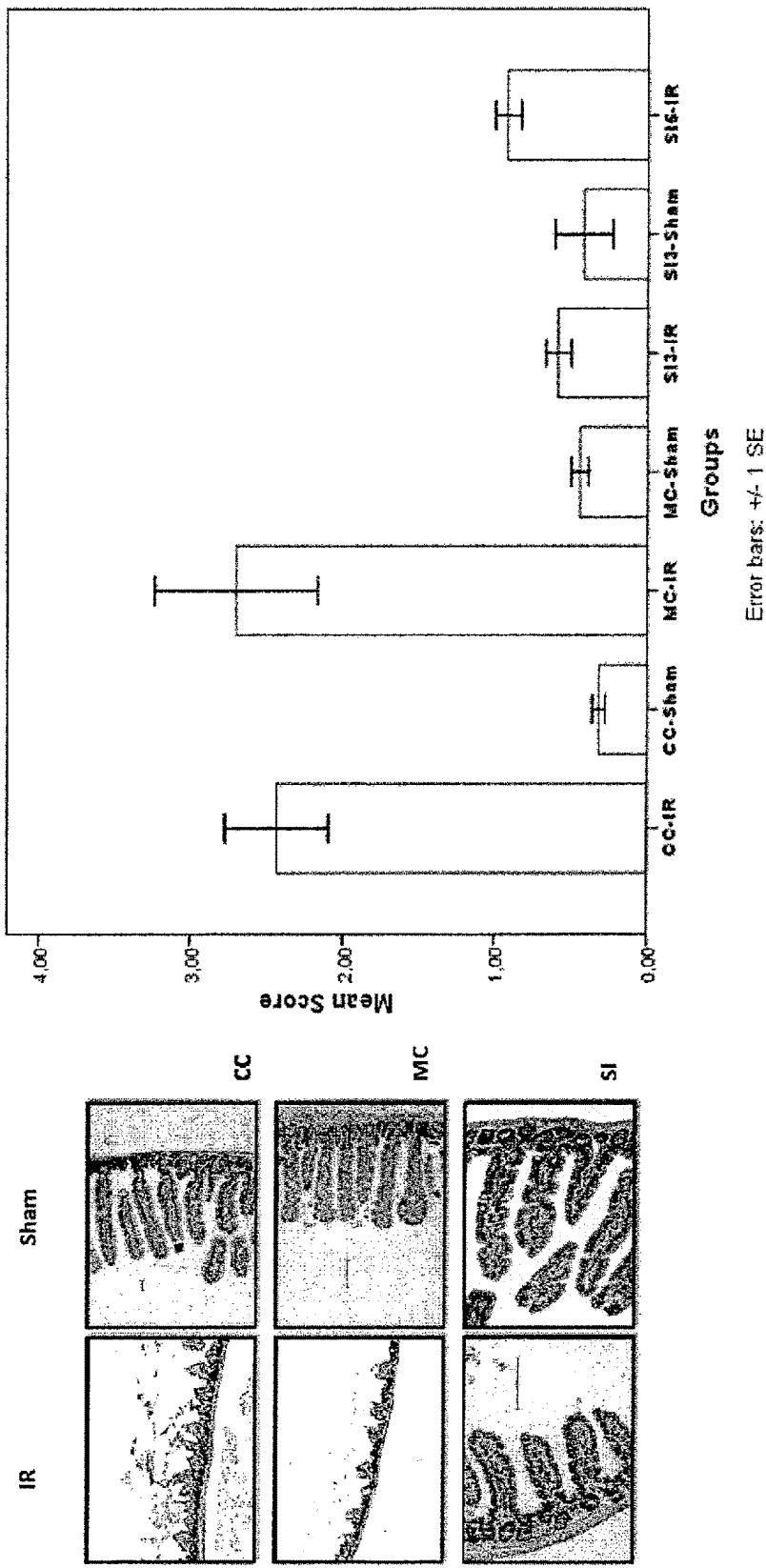

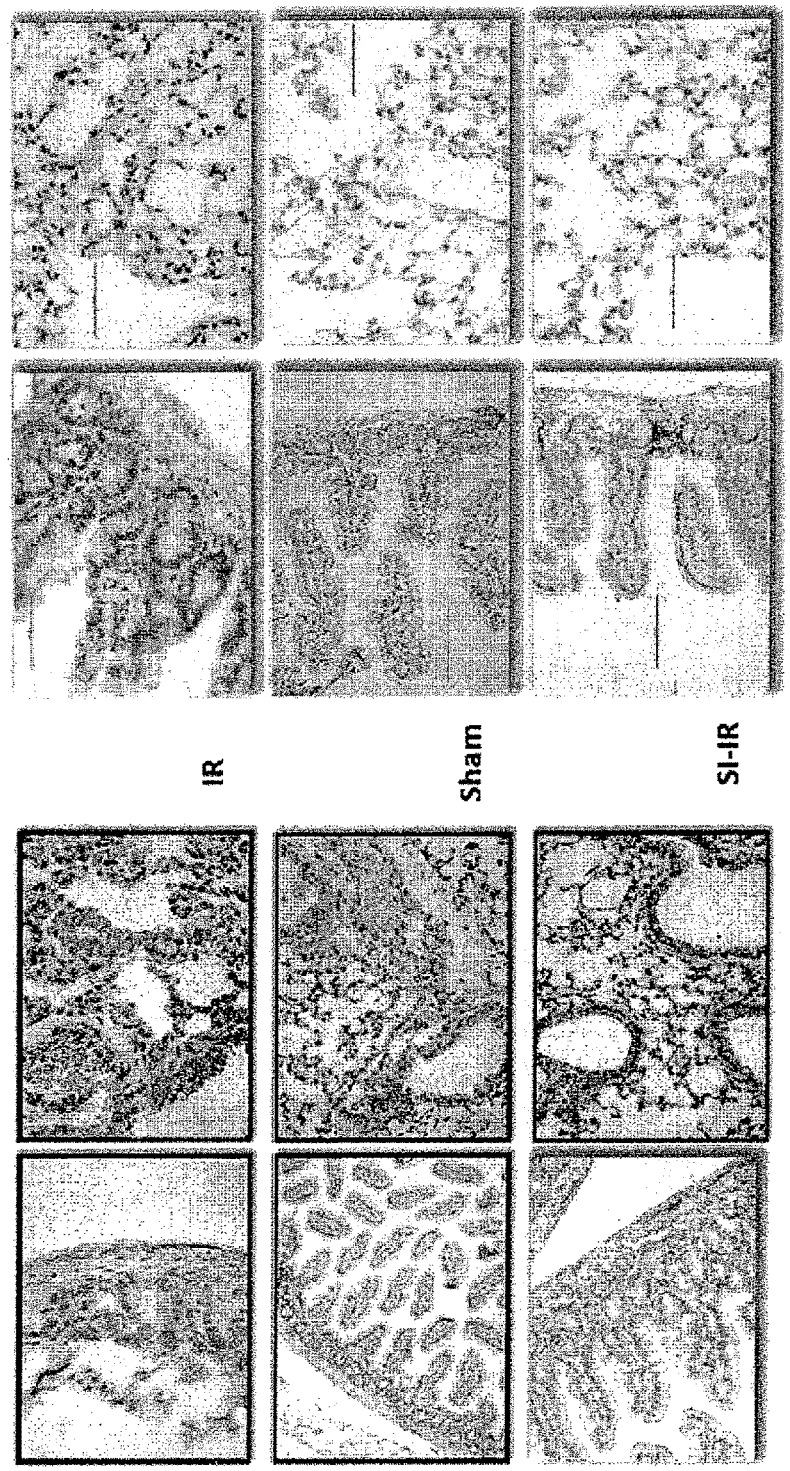

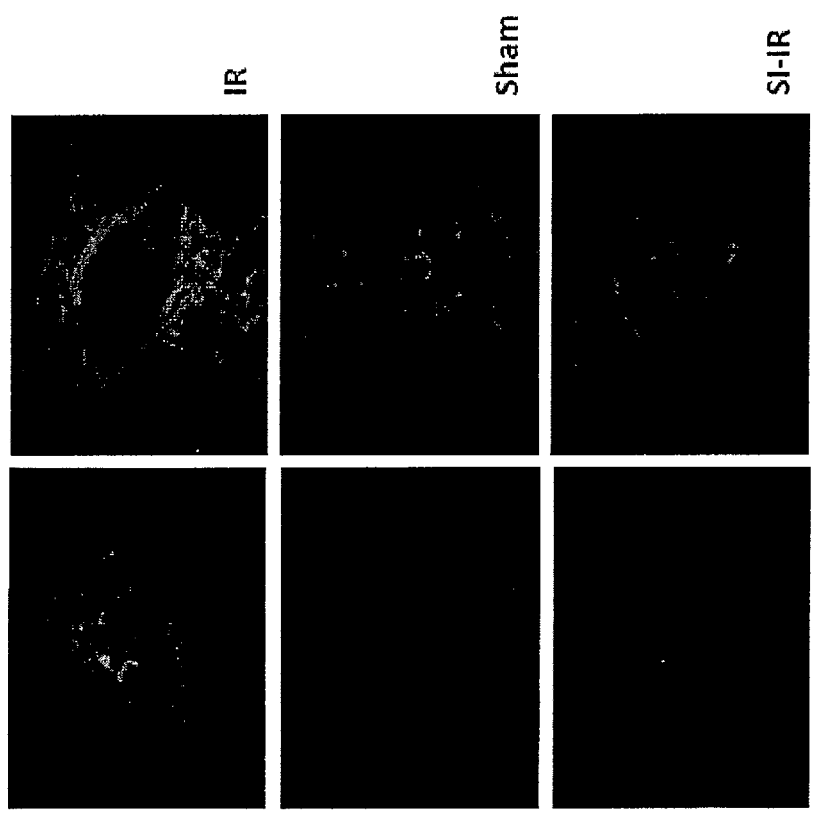

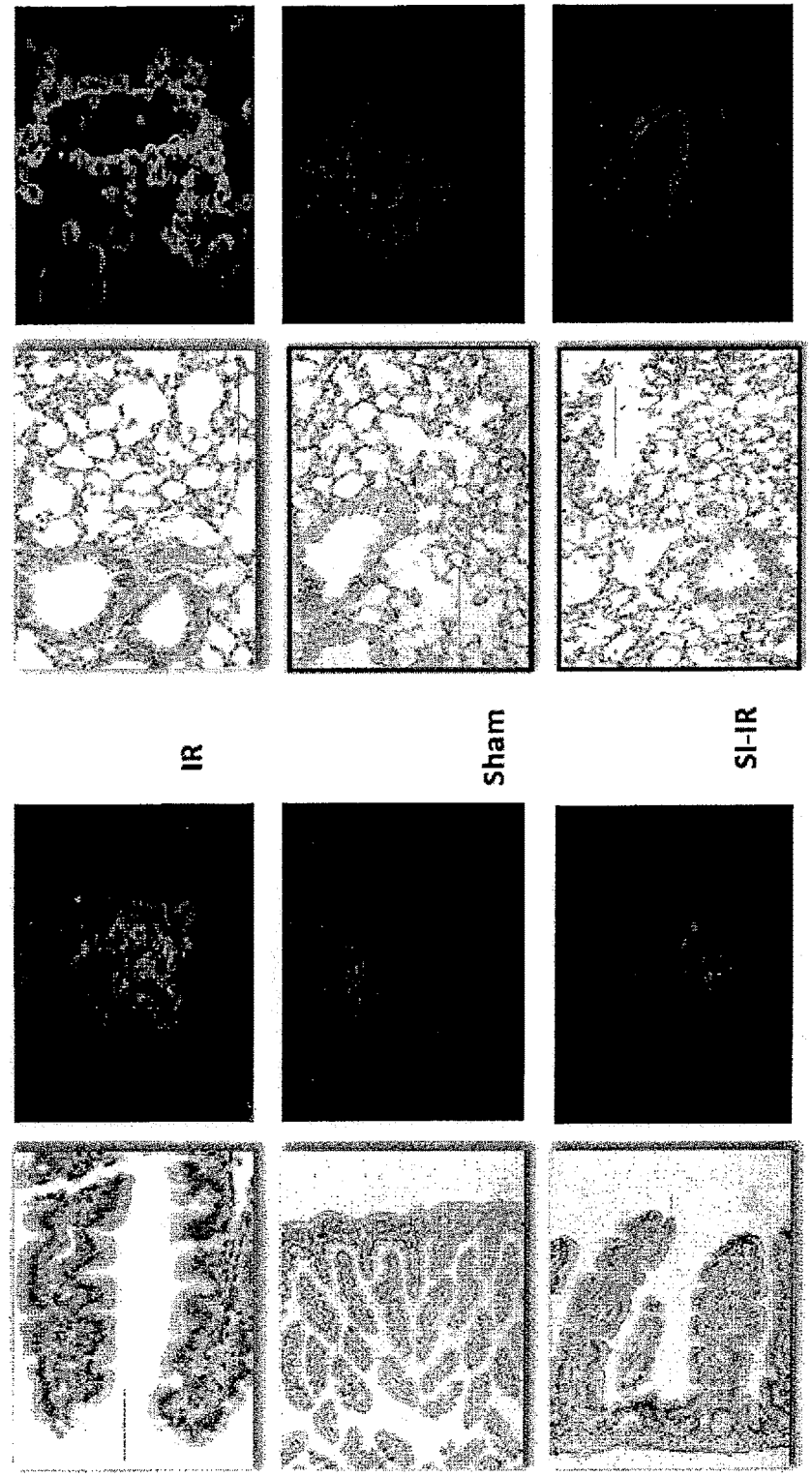

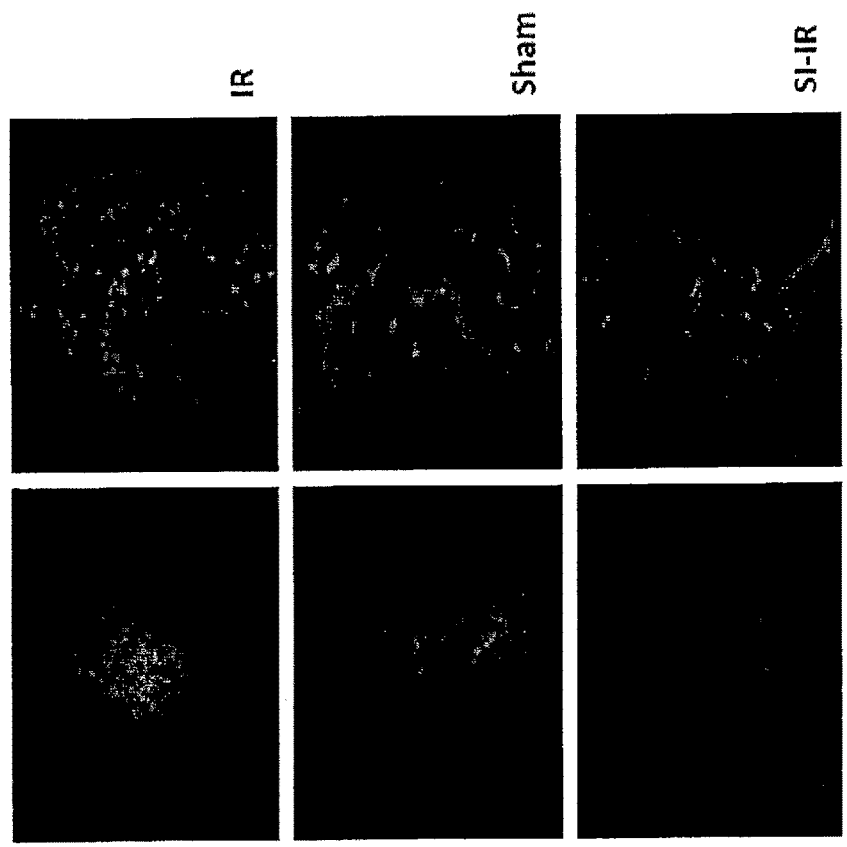

METHODS FOR TREATING ISCHEMIA-REPERFUSION INJURY

CROSS-REFERENCE TO RELATED APPLICATIONS

This application claims benefit of U.S. Provisional Application No. 61/394,560, filed Oct. 19, 2010, which is hereby incorporated by reference.

STATEMENT AS TO FEDERALLY SPONSORED RESEARCH

This invention was made with government support under grant number W81XWH-09-1-0530 from Medical Research and Material Command of the Department of the Army. The government has certain rights in the invention.

BACKGROUND OF THE INVENTION

In general, the invention is related to methods for treating, ameliorating, or attenuating an ischemia-reperfusion injury.

Ischemia-reperfusion (I/R) injury represents a leading cause of morbidity and mortality and is a major clinical problem. Reperfusion of tissues and organs subjected to ischemia or hypoperfusion elicits an inflammatory response, resulting in damage and malfunction of the affected tissues and organs. I/R injury occurs in response to a variety of clinical conditions including, e.g., shock, organ transplantation, myocardial infarction, stroke, and systemic autoimmune diseases (e.g., rheumatoid arthritis and systemic lupus erythematosus). Current therapies for ischemic disease are directed at the restoration of blood flow to the ischemic region. However, during reperfusion, additional damage may occur due to the generation of reactive oxygen species.

Thus, there exists a need in the art for methods of treating ischemia-reperfusion injury.

SUMMARY OF THE INVENTION

The present invention features methods for treating, reducing the likelihood of, or attenuating an ischemia-reperfusion injury in a subject by administering an inhibitor of spleen tyrosine kinase (Syk). Also included in the present invention are methods for identifying compounds that inhibit Syk for the treatment of an ischemia-reperfusion injury.

In one aspect, the invention features a method of treating or reducing the likelihood of an ischemia-reperfusion injury in a subject (e.g., a human subject) by providing to a subject an inhibitor of spleen tyrosine kinase (Syk) in an amount and for a duration that together are sufficient to treat or reduce the likelihood of a ischemia-reperfusion injury in the subject.

In a second aspect, the invention features a method of attenuating ischemia-reperfusion injury in a subject (e.g., a human subject) in need thereof by providing to a subject an inhibitor of Syk in an amount and for a duration that together are sufficient to attenuate a ischemia-reperfusion injury in a subject.

Ischemia-reperfusion injury may be the result of an inflammatory disorder, myocardial infarction, atherosclerosis, peripheral vascular disorder, a pulmonary embolus, a venous thrombosis, a transient ischemic attack, unstable angina, cerebral vascular ischemia, stroke, an ischemic neurological disorder, ischemic kidney disease, vasculitis, transplantation, endarterectomy, aneurysm repair surgery, or traumatic injury.

In certain embodiments of the invention, a Syk inhibitor is provided prior to the onset of an ischemia-reperfusion injury. In other embodiments, a Syk inhibitor is provided concurrently with the onset of an ischemia-reperfusion injury. In other embodiments, a Syk inhibitor is provided after the onset of an ischemia-reperfusion injury.

In certain embodiments, the Syk inhibitor of the present invention may reduce or inhibit the biological activity (e.g., kinase activity) or expression level of a Syk protein or nucleic acid molecule.

The Syk inhibitor may be a small molecule (e.g., R406 or fostamatinib) or nucleic acid (e.g., siRNA) that is provided orally, intravenously, or parenterally.

The methods of the first or second aspects may further include providing an additional therapeutic agent to a subject. The additional therapeutic agent may be, for example, an anti-inflammatory agent, a vasodilator, a beta blocker, a statin, a calcium channel blocker, an angiotensin-converting enzyme inhibitor, ranolazine, or an anticoagulant.

In a third aspect, the invention features a method of identifying a candidate compound useful for treating, reducing the likelihood, or attenuating ischemia-reperfusion injury in a subject by contacting a Syk polypeptide, or a fragment thereof, with a compound and measuring the biological activity (e.g., kinase activity) of the Syk polypeptide, or fragment thereof. A decrease in Syk biological activity in the presence of the compound relative to Syk biological activity in the absence of the compound identifies the compound as a candidate compound for treating an ischemia-reperfusion injury in a subject.

By "an amount sufficient" or "therapeutic amount" is meant the amount of a compound or therapeutic agent, alone or in combination with another compound, therapeutic agent, or therapeutic regimen, required to treat or ameliorate a condition or disorder, such as an ischemia-reperfusion injury, in a clinically relevant manner. A sufficient amount of a compound or therapeutic agent used to practice the present invention for therapeutic treatment of, e.g., an ischemia-reperfusion injury varies depending upon the manner of administration, age, and general health of the subject. Ultimately, the medical practitioner prescribing such treatment will decide the appropriate amount and dosage regimen. Additionally, a sufficient amount may be an amount of compound in a combination of therapeutic agents that is safe and efficacious in the treatment of a subject having a condition or disorder over each agent alone.

By "attenuating" is meant decreasing or otherwise reducing and includes preventing and partially reversing. As used herein, attenuating ischemia-reperfusion injury has, in some instances, the effect of decreasing and/or reducing this type of injury. In other instances, attenuating ischemia-reperfusion injury has the effect of partially reversing the injury. Partially reversing ischemia-reperfusion injury can occur when administration of, for example, a Syk inhibitor reverses ischemic damage already present in a subject being treated. "Preventing" or "reducing the likelihood of" ischemia-reperfusion injury can occur when administration of a Syk inhibitor prevents any amount or degree (e.g., from about 1% to about 100%) of possible ischemia-reperfusion injury.

By "candidate compound" or "compound" is meant a chemical, e.g., naturally-occurring or artificially-derived. Candidate compounds may include, for example, peptides, polypeptides, synthetic organic molecules, naturally-occurring organic molecules, nucleic acid molecules (e.g., siRNA), peptide nucleic acid molecules, and components and derivatives thereof.

Compounds useful in the invention include those described herein in any of their pharmaceutically acceptable forms, including isomers, such as diastereomers and enantiomers, salts, solvates, and polymorphs thereof, as well as racemic mixtures. Compounds useful in the invention may also be isotopically labeled compounds. Useful isotopes include hydrogen, carbon, nitrogen, oxygen, phosphorus, fluorine, and chlorine, (e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl). Isotopically labeled compounds can be prepared by synthesizing a compound using a readily available isotopically labeled reagent in place of a non-isotopically labeled reagent.

By "fragment" is meant a portion of a nucleic acid or polypeptide that contains at least, e.g., 10%, 20%, 30%, 40%, 50%, 60%, 70%, 80%, 90%, 95%, or more of the entire length of the nucleic acid or polypeptide (e.g., Syk nucleic acid or polypeptide). A nucleic acid fragment may contain, e.g., 10, 20, 30, 40, 50, 60, 70, 80, 90, or 100, 200, 300, 400, 500, 600, 700, 800, 900, 1000, 1100, 1200, 1300, 1400, 1500, 2000, 2500, 3000, 4000, 4500, or 5000 nucleotides or more nucleotides, up to the full length of the nucleic acid. A polypeptide fragment may contain, e.g., 10, 20, 30, 40, 50, 60, 70, 80, 90, 100, 150, 200, 250, 300, 350, 400, 450, or 500 amino acids or more amino acids, up to the full length of the polypeptide. Fragments useful in the therapeutic methods of the invention include, e.g., fragments that retain biological activity. Fragments can be modified as described herein and as known in the art.

By "inhibitor" is meant any compound (i.e., peptidyl or non-peptidyl), small molecule, antibody, nucleic acid molecule, polypeptide, or fragment thereof that reduces or inhibits the expression levels or biological activity of a protein or nucleic acid molecule by at least 10%, 20%, 30%, 40%, 50%, 60%, 70%, 80%, 90%, 95%, 99% or more. Non-limiting examples of inhibitor compounds include dominant negative fragments or mutant polypeptides that block the biological activity of the wild-type protein; peptidyl or non-peptidyl compounds (e.g., antibodies or antigen-binding fragments thereof) that bind to a protein, for example at a functional domain or substrate binding domain; antisense nucleobase oligomers; morpholinos; double-stranded RNA for RNA interference; small molecule inhibitors; compounds that decrease the half-life of an mRNA or protein; and compounds that decrease transcription or translation of a polypeptide.

By "ischemia-reperfusion injury" or "I/R injury" is meant damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function. I/R injury may occur in a wide variety of organs and tissues including, but not limited to, the brain and other nervous tissue (e.g., the retina and spinal cord), liver, stomach, intestines, kidney, lung, skin, skeletal muscle, and pancreas. Such injury may be the result of any ischemic disorder including, e.g., an inflammatory disorder (e.g., rheumatoid arthritis or system lupus erythematosus), myocardial infarction, atherosclerosis, peripheral vascular disorder, a pulmonary embolus, a venous thrombosis, a transient ischemic attack, unstable angina, cerebral vascular ischemia, stroke, an ischemic neurological disorder, ischemic kidney disease, vasculitis, endarterectomy, aneurysm repair surgery, traumatic injury, or surgery involving organ or tissue transplantation.

By "pharmaceutically acceptable carrier" is meant a carrier that is physiologically acceptable to the treated subject while retaining the therapeutic properties of the composition with which it is administered. One exemplary pharmaceutically acceptable carrier substance is physiological saline. Other physiologically acceptable carriers and their formulations are known to one skilled in the art and are described, for example, in Remington's Pharmaceutical Sciences (20$^{th}$ edition, A. Gennaro, ed., 2000, Lippincott, Williams & Wilkins, Philadelphia, Pa.).

By "protein," "polypeptide," "polypeptide fragment," or "peptide" is meant any chain of two or more amino acid residues, regardless of post-translational modification (e.g., glycosylation or phosphorylation), constituting all or part of a naturally occurring polypeptide or peptide or constituting a non-naturally occurring polypeptide or peptide. A polypeptide or peptide may be said to be "isolated" or "substantially pure" when physical, mechanical, or chemical methods have been employed to remove the polypeptide from cellular constituents. An "isolated polypeptide," "substantially pure polypeptide," or "substantially pure and isolated polypeptide" is typically considered removed from cellular constituents and substantially pure when it is at least 60% by weight free from the proteins and naturally occurring organic molecules with which it is naturally associated. The polypeptide may be at least 75%, 80%, 85%, 90%, 95%, or 99% by weight pure. A substantially pure polypeptide may be obtained by standard techniques, for example, by extraction from a natural source (e.g., cell lines or biological fluids), by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis. Alternatively, a polypeptide is considered isolated if it has been altered by human intervention, placed in a location that is not its natural site, or if it is introduced into one or more cells.

The peptides and polypeptides of the invention, as defined above, include all "mimetic" and "peptidomimetic" forms. The terms "mimetic" and "peptidomimetic" refer to a synthetic chemical compound that has substantially the same structural and/or functional characteristics of the peptides or polypeptides of the invention. The mimetic can be either entirely composed of synthetic, non-natural analogs of amino acids or may be a chimeric molecule of natural amino acids and non-natural analogs of amino acids. The mimetic can also incorporate any amount of conservative substitutions, as long as such substitutions do not substantially alter the mimetic's structure or activity.

By "reduce or inhibit" is meant the ability to cause an overall decrease of 20% or greater, of 50% or greater, or of 75%, 80%, 85%, 90%, 95%, or greater. For therapeutic applications, to "reduce or inhibit" can refer to the symptoms of the disorder being treated or the presence or extent of a condition or disorder being treated. For diagnostic or monitoring applications, to "reduce or inhibit" can refer to a decrease in the level of protein or nucleic acid detected by the diagnostic or monitoring assays.

By "reducing the likelihood of" is meant reducing the severity, the frequency, and/or the duration of a condition or disorder (e.g., an ischemic-reperfusion injury) or symptoms thereof. Reducing the likelihood of an ischemia-reperfusion injury is synonymous with prophylaxis or the chronic treatment of an ischemia-reperfusion injury.

By "subject" is meant a mammal, including, but not limited to, a human or non-human mammal, such as a bovine, equine, canine, ovine, or feline.

By "spleen tyrosine kinase" or "Syk" is meant a polypeptide, or a nucleic acid sequence that encodes it, or fragments or derivatives thereof, that is substantially identical or homologous to or encodes any protein substantially identical to the amino acid set forth in NCBI Accession No. NP_003168.2 (isoform 1) or NCBI Accession No. NP_001128524.1 (isoform 2). Syk can also include fragments, derivatives, homologs, orthologs, or analogs of Syk that retain at least 10%, 15%, 20%, 25%, 30%, 40%, 50%, 60%, 70%, 80%, 90%, 95%, 96%, 97%, 98%, 99%, or more Syk biological activity. The Syk polypeptides may be isolated from a variety of sources, such as from mammalian tissue, plasma, or cells, or from another source, or prepared by recombinant or synthetic methods. The term "Syk" also encompasses modifications to the polypeptide, fragments, derivatives, analogs, and variants of the Syk polypeptide having Syk biological activity.

By "Syk biological activity" is meant any of the following activities: kinase activity, transmission of signals from cell receptors (e.g., B-cell, T-cell and Fc receptors, integrins, and CD74), or cell signaling (e.g., osteoclast, monocyte, or mast cell signaling).

By "Syk inhibitor" is meant any compound which inhibits the biological activity of Syk or expression of Syk. A Syk inhibitor may inhibit the kinase activity of Syk or any other biological activity of Syk described herein. Compounds may be identified as Syk inhibitors by evaluating the compounds in assays known to one of skill in the art and described herein. Known inhibitors of Syk include, for example, R406 (N4-(2,2-dimethyl-3-oxo-4H-pyrid[1,4]oxazin-6-yl)-5-fluoro-N2-(3,4,5-trimethoxyphenyl)-2,4-pyrimidinediamine), R733 (fostamatinib), and substituted [1,6]-naphthyridines.

By "treating" or "ameliorating" is meant administering a composition (e.g., a pharmaceutical composition) for therapeutic purposes or administering treatment to a subject already suffering from a condition or disorder to improve the subject's condition. By "treating a condition or disorder" or "ameliorating a condition or disorder" is meant that the condition or disorder and/or the symptoms associated with the condition or disorder are, e.g., alleviated, reduced, cured, or placed in a state of remission.

Other features and advantages of the invention will be apparent from the detailed description and from the claims.

BRIEF DESCRIPTION OF THE SEVERAL VIEWS OF THE DRAWINGS

FIGS. 1A-1B show that Syk inhibitor therapy attenuates ischemia-reperfusion (I/R) injury in the intestine. FIG. 1A is a series of representative hematoxylin and eosin (H&E)-stained slides from the intestine of mice subjected to an I/R or sham operation and treated with Syk inhibitor (3 g/kg and 5 g/kg for 6 days) visualized and captured under a light microscope. FIG. 1B is a bar graph showing the scoring of H&E-stained intestinal sections from different treatment groups for intestinal mucosal damage. Data were compared using ANOVA followed by the Tukey's multiple comparison test (CC: control chow, MC: mouse chow, and SI: Syk inhibitor).

FIG. 2A is a series of representative H&E-stained paraffin sections of lung tissue, subjected to the same treatment as the tissue in FIG. 1A. FIG. 2B is a bar graph showing the scoring of lung injury from each group, as described in the Examples. Data were compared using ANOVA followed by the Tukey's multiple comparison test.

FIGS. 3A-3D show Syk staining in the intestine and lung tissues. Syk staining was assessed in the intestine (FIG. 3A) and lung (FIG. 3B) tissues by immunohistochemistry staining. p-Syk staining was performed in the intestine (FIG. 3C) and lung (FIG. 3D) tissues by immunohistochemistry.

FIGS. 4A-4B show that Syk inhibitor therapy reduces IgM staining. IgM staining was performed in the intestine (FIG. 4A) and lung (FIG. 4B) tissues by immunofluorescence.

FIGS. 5A-5D show that Syk inhibitor reduces I/R-exacerbated C3 deposition in the intestine and lung tissues. C3 deposition in the intestine tissue was assessed by immunohistochemistry (FIG. 5A) and immunofluorescence (FIG. 5B) staining. C3 deposition in the lung tissue was assessed by immunohistochemistry staining (FIG. 5C) and immunofluorescence staining (FIG. 5D) using confocal microscopy.

FIGS. 6A-6B show that administration of Syk inhibitor therapy decreases neutrophil infiltration. GR-1 staining was performed in the intestine (FIG. 6A) and the lung (FIG. 6B) tissues by immunofluorescence.

FIG. 7A shows a Western blot of Syk expression after cells were transfected with varying concentrations of Syk siRNA corresponding to SEQ ID NOs: 5 and 6. FIG. 7B shows a Western blot of Syk expression after cells were transfected with varying concentrations of Syk siRNA corresponding to SEQ ID NOs: 3 and 4. FIG. 7C shows a Western blot of Syk expression after cells were transfected with varying concentrations of Syk siRNA corresponding to SEQ ID NOs: 1 and 2.

DETAILED DESCRIPTION

Figure 2A:
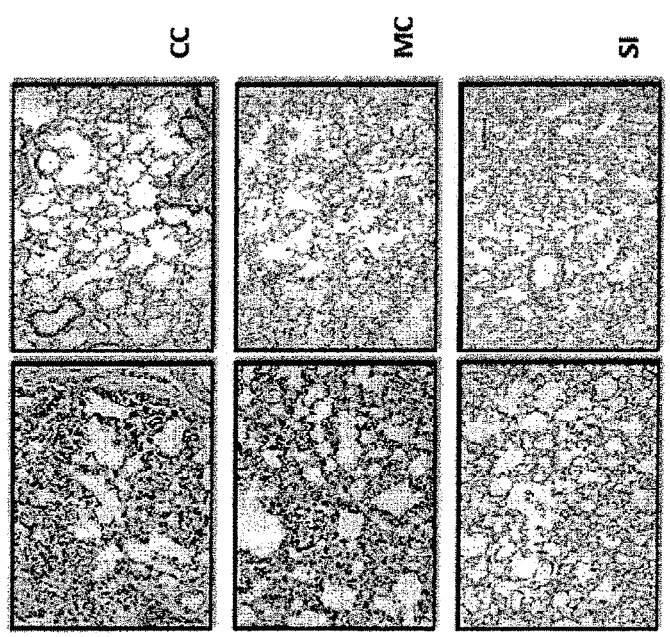
FIGS. 2A-2B show that Syk inhibitor therapy reduces remote lung injury following mesenteric I/R.

We have demonstrated that inhibition of Syk limits local and remote organ damage in mice subjected to intestinal ischemia-reperfusion injury. Thus, Syk inhibitors may be useful for the treatment, prevention, or attenuation of injury in conditions or disorders associated with reperfusion of ischemic tissues. In addition, we describe herein methods for the identification of additional Syk inhibitors.

Ischemia-Reperfusion Injury

The methods of the present invention may be used in the treatment, inhibition, or attenuation of ischemia-reperfusion injury.

To treat, inhibit, or attenuate ischemia-reperfusion injury in a subject of the invention, one or more therapeutic agents (e.g., Syk inhibitors) may be administered before, during, or after the onset of ischemia associated with any condition or disorder. In certain embodiments, a Syk inhibitor is administered to a subject at risk of ischemia-reperfusion injury.

Conditions or disorders associated with ischemia-reperfusion injury include, e.g., acute myocardial infarction, angioplasty, coronary artery bypass surgery, surgery involving organ or tissue transplantation (e.g., heart transplantation), stroke, inflammatory disorders (e.g., rheumatoid arthritis or systemic lupus erythematosus), head trauma, drowning, sepsis, atherosclerosis, hypertension (e.g., pulmonary hypertension), drug-induced heart disease, smoking-induced heart disease, heart failure, hemorrhage, capillary leak syndrome (e.g., child and adult respiratory distress syndrome), multi-organ system failure, a state of low colloid oncotic pressure (e.g., due to starvation, anorexia nervosa, or hepatic failure with decreased production of serum proteins), anaphylaxis, hypothermia, cold injury (e.g., frostbite), hepatorenal syndrome, delirium tremens, mesenteric insufficiency, peripheral vascular disease, claudication, burn, electrocution, drug-induced vasodilation, drug-induced vasoconstriction, tissue rejection after transplantation, graft versus host disease, radiation exposure, a pulmonary embolus, a venous thrombosis, a transient ischemic attack, unstable angina, cerebral vascular ischemia, an ischemic neurological disorder, ischemic kidney disease, or traumatic injury.

In one embodiment, one or more therapeutic agents of the invention are administered to treat, inhibit, or attenuate ischemia-reperfusion injury associated with a vascular interventional procedure. Vascular interventional procedures include, e.g., those which employ a stent, angioplasty catheter (e.g., percutaneous transluminal angioplasty), laser catheter, atherectomy catheter, angioscopy device, beta- or gamma-radiation catheter, intravascular ultrasound device, rotational atherectomy device, radioactive balloon, heatable wire, heatable balloon, biodegradable stent strut, or biodegradable sleeve.

Subjects who have experienced one myocardial infarction have a high risk of having subsequent myocardial infarctions. Therefore, in one embodiment, subjects who survive a myocardial infarction may be chronically treated with one or more therapeutic agents (e.g., Syk inhibitors) of the invention to decrease the risk of recurrence. Similarly, one or more agents of the invention may be administered chronically to subject with an inflammatory disorder (e.g., rheumatoid arthritis, or systemic lupus erythematosus), a subject that has had a stroke, or a subject with peripheral vascular disease.

Thus, the therapeutic agents of the invention (e.g., Syk inhibitors) can be used prophylactically in a subject after a cardiovascular event or in a subject at risk of an ischemic event. Subjects with an increased risk of experiencing an ischemia-reperfusion injury include, e.g., smokers, diabetics, subjects with hypertension or dyslipidemia, subjects with a family history of vascular events, subjects with documented coronary disease, peripheral vascular disease, or cerebrovascular disease, or subjects undergoing diagnostic or therapeutic radiation or chemotherapy.

Therapeutic Compounds

Therapeutic compounds useful in the methods of the invention include any compound that can reduce or inhibit the biological activity or expression level of, e.g., Syk.

Exemplary inhibitor compounds include, but are not limited to, peptidyl or non-peptidyl compounds that specifically bind Syk; antisense nucleobase oligomers; morpholino oligonucleotides; small RNAs; small molecule inhibitors; compounds that decrease the half-life of the mRNA or protein of Syk; compounds that decrease transcription or translation of Syk; or compounds that reduce or inhibit the expression levels Syk or decrease the biological activity of Syk.

Inhibitor compounds of the present invention may reduce or inhibit the biological activity or expression levels of Syk by at least 10%, 20%, 25%, 30%, 40%, 50%, 60%, 70%, 80%, 90%, 95%, 96%, 97%, 98%, 99%, or more. Preferably, the inhibitor compound can reduce, inhibit, or attenuate an ischemia-reperfusion injury or symptoms of an ischemia-reperfusion injury by at least 10%, 20%, 25%, 30%, 40%, 50%, 60%, 70%, 80%, 90%, 95%, 96%, 97%, 98%, 99%, or more.

Nucleic Acid Molecules

The present invention features inhibitory nucleic acid molecules that may be used for the treatment or amelioration of an ischemia-reperfusion injury. Such inhibitory nucleic acid molecules are capable of, for example, mediating down-regulation of the expression of a Syk polypeptide or nucleic acid encoding the same or mediating a decrease in the activity of Syk. Examples of the inhibitory nucleic acids of the invention include, without limitation, antisense oligomers (e.g., morpholinos), double-stranded RNAs (dsRNAs) (e.g., small interfering RNAs (siRNAs) and short hairpin RNAs (shRNAs)), and aptamers.

Antisense Oligomers

The present invention features the use of antisense nucleobase oligomers to downregulate expression of mRNA encoding a polypeptide (e.g., Syk). By binding to the complementary nucleic acid sequence (the sense or coding strand), antisense nucleobase oligomers are able to inhibit protein expression. For example, the antisense nucleobase oligomer may reduce Syk polypeptide expression in a cell that expresses increased levels of Syk by at least 10%, 20%, 30%, 40%, 50%, 60%, 70%, 80%, 90%, or greater relative to cells treated with a control oligonucleotide. Methods for selecting and preparing antisense nucleobase oligomers are well known in the art. Methods for assaying levels of protein expression are also well known in the art and include, for example, Western blotting, immunoprecipitation, and ELISA.

One example of an antisense nucleobase oligomer particularly useful in the methods and compositions of the invention is a morpholino oligomer. Morpholinos act by binding to a target sequence within an RNA and blocking molecules which might otherwise interact with the RNA. Therefore, morpholinos directed to a Syk polypeptide that reduce or inhibit the expression levels or biological activity of Syk are particularly useful in the methods of the invention that require the use of inhibitor compounds.

dsRNAs

The present invention also features the use of double-stranded RNAs including, but not limited to, siRNAs and shRNAs. Short, double-stranded RNAs may be used to perform RNA interference (RNAi) to inhibit the expression of a polypeptide of the invention (e.g., Syk). RNAi is a form of post-transcriptional gene silencing initiated by the introduction of dsRNA. Short (e.g., 15 to 32) nucleotide double-stranded RNAs, known generally as "siRNAs," "small RNAs," or "microRNAs," are effective at down-regulating gene expression in nematodes (Zamore et al., *Cell* 101: 25-33) and in mammalian tissue culture cell lines (Elbashir et al., *Nature* 411:494-498, 2001). The further therapeutic effectiveness of this approach in mammals was demonstrated in vivo by McCaffrey et al. (*Nature* 418: 38-39, 2002). The small RNAs are at least 10 nucleotides, preferably 11, 12, 13, 14, 15, 16, 17, 18, 19, 20, 21, 22, 23, 24, 25, 26, 27, 28, 29, 30, 31, 32, 33, 34, or 35 nucleotides in length and even up to 50 or 100 nucleotides in length (inclusive of all integers in between). Such small RNAs that are substantially identical to or complementary to any region of a polypeptide described herein are included in the invention. Non-limiting examples of small RNAs are substantially identical to (e.g., 60%, 65%, 70%, 75%, 80%, 85%, 90%, 95%, 96%, 97%, 98%, 99%, or 100% sequence identity) or complementary to the Syk nucleic acid sequence (e.g., the human Syk nucleic acid sequence (NCBI Accession No. NM_001174167.1 (isoform 1) or NCBI Accession No. NM_001135052.2 (isoform 2))). It should be noted that longer dsRNA fragments that are processed into small RNAs may be used. Small RNAs to be used as inhibitors of the invention can be identified by their ability to decrease polypeptide expression levels or biological activity performing assays known in the art or provided herein.

The specific requirements and modifications of small RNAs are known in the art and are described, for example, in PCT Publication No. WO 01/75164 and U.S. Patent Application Publication Nos. 2006/0134787, 2005/0153918, 2005/0058982, 2005/0037988, and 2004/0203145, the relevant portions of which are herein incorporated by reference.

siRNA molecules can be obtained and purified through a variety of protocols known to one of skill in the art, including chemical synthesis or recombinant production using a *Drosophila* in vitro system. They are commercially available from companies such as Dharmacon Research, Inc. or Xeragon, Inc., or they can be synthesized using commercially available kits such as the Silencer™ siRNA Construction Kit from Ambion or HiScribe™ RNAi Transcription Kit from New England BioLabs. Alternatively, siRNA can be prepared using standard procedures for in vitro transcription of RNA and dsRNA annealing procedures. Exemplary pairs of Syk-specific siRNA include:

```
Sense:
                             (SEQ ID NO: 1)
GGAUAAGAACAUCAUAGAAtt

Antisense:
                             (SEQ ID NO: 2)
UUCUAUGAUGUUCUUAUCCtt

Sense:
                             (SEQ ID NO: 3)
CGCUCUUAAAGAUGAGUUAtt

Antisense:
                             (SEQ ID NO: 4)
UAACUCAUCUUUAAGAGCGgg

Sense:
                             (SEQ ID NO: 5)
GCACUAUCGCAUCGACAAAtt

Antisense:
                             (SEQ ID NO: 6)
UUUGUCGAUGCGAUAGUGCag
``` shRNAs can also be used in the methods of the invention. shRNAs are designed such that both the sense and antisense strands are included within a single RNA molecule and connected by a loop of nucleotides. shRNAs can be synthesized and purified using standard in vitro T7 transcription synthesis. shRNAs can also be subcloned into an expression vector, which can then be transfected into cells and used for in vivo expression of the shRNA.

A variety of methods are available for transfection of dsRNA into mammalian cells. For example, there are several commercially available transfection reagents useful for lipid-based transfection of siRNAs including, but not limited to, TransIT-TKO™ (Mirus), Transmessenger™ (Qiagen), Oligofectamine™ and Lipofectamine™ (Invitrogen), siPORT™ (Ambion), and DharmaFECT™ (Fisher Scientific). Agents are also commercially available for electroporation-based methods for transfection of siRNA, such as siPORTer™ (Ambion). Microinjection techniques may also be used. The small RNA can also be transcribed from an expression construct introduced into the cells, where the expression construct includes a coding sequence for transcribing the small RNA operably linked to one or more transcriptional regulatory sequences. Where desired, plasmids, vectors, or viral vectors can also be used for the delivery of dsRNA or siRNA, and such vectors are known in the art. Protocols for each transfection reagent are available from the manufacturer. Additional methods are known in the art and are described, for example, in U.S. Patent Application Publication No. 2006/0058255.

Aptamers

The present invention also features aptamers to the polypeptides of the invention (e.g., Syk) and the use of such aptamers to down-regulate expression of the polypeptide or nucleic acid encoding the polypeptide. Aptamers are nucleic acid molecules that form tertiary structures that specifically bind to a target molecule. The generation and therapeutic use of aptamers are well established in the art. See, e.g., U.S. Pat. No. 5,475,096 and U.S. Patent Application Publication No. 2006/0148748. For example, a Syk aptamer may be a PEGylated, modified oligonucleotide, which adopts a three-dimensional conformation that enables it to bind to Syk and inhibit the biological activity of Syk.

Small Molecule Therapeutic Agents

Small molecule therapeutic agents for use in the present invention can be identified using standard screening methods specific to the target (e.g., Syk). These screening methods can also be used to confirm the activities of derivatives of compounds found to have a desired activity, which are designed according to standard medicinal chemistry approaches. After a small molecule therapeutic agent is confirmed as being active with respect to a particular target, the therapeutic agent can be tested in vitro, as well as in appropriate animal model systems.

Examples of small molecule therapeutic agents (e.g., inhibitors of Syk) that may be used in the methods of the present invention include, e.g., R406 (N4-(2,2-dimethyl-3-oxo-4H-pyrid[1,4]oxazin-6-yl)-5-fluoro-N2-(3,4,5-trimethoxyphenyl)-2,4-pyrimidinediamine), R733 (fostamatinib), and substituted [1,6]-naphthyridines, and any derivatives, analogs, or mimetics thereof. Additional Syk inhibitors and methods of making such inhibitors are known in the art and are described, for example, in Braselmann et al., *J Pharmacol Exp Ther.* 319: 998-1008, 2006; Cha et al., *J Pharmacol Exp Ther.* 317: 571-578, 2006; and U.S. Pat. Nos. 7,321,041; 7,435,814; 7,449,458; 7,485,724; 7,498,435; 7,538,108; 7,563,892; 7,642,351; 7,655,797; 7,678,911; and 7,705,151.

Therapeutic Administration and Formulation

The therapeutic agents described herein (e.g., inhibitors of Syk) can be formulated and administered in a variety of ways (e.g., routes known for specific indications, including, but not limited to, topically, orally, subcutaneously, bronchial injection, intravenously, intracerebrally, intranasally, transdermally, intraperitoneally, intramuscularly, intrapulmonary, vaginally, rectally, intraarterially, intralesionally, parenterally, intraventricularly in the brain, or intraocularly). For example, a pharmaceutical composition containing an inhibitor of Syk may be in the form of a pill, tablet, capsule, liquid, or sustained-release tablet for oral administration; a liquid for intravenous or subcutaneous administration; a polymer or other sustained-release vehicle for local administration; or an ointment, cream, gel, liquid, or patch for topical administration. Continuous systemic infusion or periodic injection of the therapeutic agent (e.g., inhibitor of Syk) can also be used to treat, ameliorate, attenuate, or reduce the likelihood of a condition or disorder (e.g., an ischemia-reperfusion injury).

For parenteral administration, the therapeutic agents may be formulated in a unit dosage injectable form (e.g., solution, suspension, or emulsion) in association with a pharmaceutically acceptable parenteral vehicle. Such vehicles are inherently non-toxic and non-therapeutic. Examples of such vehicles include, e.g., water, saline, Ringer's solution, dextrose solution, liposomes, and 5% human serum albumin. Nonaqueous vehicles, such as fixed oils and ethyl oleate, may also be used. The vehicle may contain minor amounts of additives, such as substances that enhance isotonicity and chemical stability (e.g., buffers and preservatives). Therapeutic agents typically are formulated in such vehicles at concentrations of about 1 mg/ml to 10 mg/ml.

Where sustained release administration of the therapeutic agent is desired in a formulation with release characteristics suitable for the treatment or attenuation of, e.g., an ischemia-reperfusion injury, microencapsulation of the therapeutic agent may be contemplated. See, e.g., Johnson et al., *Nat Med.* 2: 795-799, 1996; Yasuda, *Biomed Ther.* 27: 1221-1223, 1993; Hora et al., *Bio/Technology* 8: 755-758 1990; Cleland, "Design and Production of Single Immunization Vaccines Using Polylactide Polyglycolide Microsphere Systems," in "Vaccine Design: The Subunit and Adjuvant Approach," Powell and Newman, Eds., Plenum Press: New York, pp. 439-462, 1995; WO 97/03692; WO 96/40072; WO 96/07399; and U.S. Pat. No. 5,654,010, hereby incorporated by reference.

Sustained-release formulations may include those developed using poly-lactic-coglycolic acid (PLGA) polymer. The degradation products of PLGA, lactic acid and glycolic acid, can be cleared quickly from the human body. Moreover, the degradability of this polymer can be adjusted from months to years depending on its molecular weight and composition (see, e.g., Lewis, "Controlled release of bioactive agents from lactide/glycolide polymer," in M. Chasin and Dr. Langer (Eds.), Biodegradable Polymers as Drug Delivery Systems (Marcel Dekker: New York, pp. 1-41, 1990).

Therapeutic formulations are prepared using standard methods known in the art by mixing the active ingredient having the desired degree of purity with optional physiologically acceptable carriers, excipients, or stabilizers in the form of lyophilized formulations or aqueous solutions (see, e.g., Remington's Pharmaceutical Sciences, 20$^{th}$ edition, A. Gennaro, ed., 2000, Lippincott, Williams & Wilkins, Philadelphia, Pa.). Acceptable carriers include, e.g., saline; buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagines, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

The therapeutic formulation may contain a pharmaceutically acceptable salt (e.g., sodium chloride), preferably at a physiological concentration. The formulations of the invention can also contain a pharmaceutically acceptable preservative. In some embodiments, the preservative concentration ranges from 0.1 to 2.0% v/v. Suitable preservatives include those known in the pharmaceutical arts (e.g., benzyl alcohol, phenol, m-cresol, methylparaben, and propylparaben). The formulations of the invention may also include a pharmaceutically acceptable surfactant (e.g., non-ionic detergents, Tween-20, or pluronic acid (F68)). Suitable surfactant concentrations are, e.g., 0.005 to 0.02%.

Administrations can be single or multiple administrations (e.g., 2-, 3-, 6-, 8-, 10-, 20-, 50-, 100-, 150-, or more administrations). The composition can be administered at anytime (e.g., after diagnosis or detection of a disorder or a condition associated with the disorder (e.g., using the diagnostic methods known in the art or described herein) or before diagnosis of a disorder to a subject at risk of developing the disorder). Encapsulation of the therapeutic agent (e.g., inhibitor of Syk) in a suitable delivery vehicle (e.g., polymeric microparticles or implantable devices) may increase the efficiency of delivery, particularly for oral delivery.

Administration of a therapeutic agent, alone or in combination with another therapeutic agent, can be one to four times daily for one day to one year, for example, 1 to 100 days, 1 to 60 days, or until the symptoms of the disorder are reduced or eliminated, and may even be for the life of the subject. Chronic, long-term administration may be required in some cases.

Dosages

Generally, when administered to a human, the dosage of any of the therapeutic agents (e.g., inhibitors of Syk) described herein may depend on the nature of the agent and can readily be determined by one skilled in the art. Typically, such dosage is about 0.001 mg to 2000 mg per day, about 1 mg to 1000 mg per day, or about 5 mg to 500 mg per day. In certain embodiments, the therapeutic agent is the Syk inhibitor R406 or R788, and R406 or R788 is administered in a dosage of about 100 or 150 mg twice daily.

The dosage required depends on the choice of the route of administration; the nature of the formulation; the nature of the subject's disorder; the subject's size, weight, surface area, age, and sex; other drugs being administered; and the judgment of the subject's physician. Wide variations in the needed dosage are to be expected in view of the differing efficiencies of various routes of administration. For example, oral administration would be expected to require higher dosages than administration by intravenous injection. Variations in these dosage levels can be adjusted using standard empirical routines for optimization, as is well understood in the art. Additionally, pharmacogenomic information (e.g., the effect of genotype on the pharmacokinetic, pharmacodynamic, or efficacy profile of a therapeutic) about a particular subject may affect the dosage used.

Combination Therapies

The therapeutic agent(s) (e.g., an inhibitor of Syk) of the present invention may be provided in conjunction with (e.g., before, during, or after) additional therapies to treat a condition or disorder (e.g., an ischemia-reperfusion injury). Treatment therapies that can be used in combination with the methods of the invention include, but are not limited to, anti-inflammatory agents (e.g., aspirin, ibuprofen, ketoprofen, piroxicam, indomethacin, diclofenac, sulindac, naproxen, or celecoxib), vasodilators (e.g., nitroglycerin), beta blockers (e.g., alprenol, bucindolol, cartelol, carvedilol, nadolol, pindolol, propranolol, atenolol, bisoprolol, metoprolol, nebivolol, acebutolol, betaxolol, or butaxamine), cholesterol-lowering medications (e.g., statins, fibrates, nicotinic acid, bile-acid resins, or cholesterol absorption inhibitors), calcium channel blockers (e.g., lomerizine or bepridil), angiotensin-converting enzyme (ACE) inhibitors (e.g., benazepril, captopril, enalapril, fosinopril, lisinopril, moexipril, perindopril, quinapril, ramipril, or trandolapril), ranolazine, or anticoagulants (e.g., coumadins or heparins).

In addition to the administration of therapeutic agents, the additional therapeutic regimen may involve, e.g., gene therapy, surgery (e.g., coronary artery bypass surgery, angioplasty, and/or stenting), or a modification to the lifestyle of the subject being treated. Such lifestyle changes may be helpful to prevent an ischemia-reperfusion injury and include weight loss, physical exercise, diet control, reduction in alcohol intake, and reduction in smoking.

Screening Assays

The methods of the present invention also include screening methods to identify compounds that modulate, alter, or decrease (e.g., by at least 10%, 20%, 30%, 40%, 50%, 60%, 70%, 80%, 90%, 95%, or more) the expression or biological activity of Syk. Compounds that decrease the expression or biological activity of Syk may be used for the treatment, amelioration, or attenuation of ischemia-reperfusion injury. Candidate compounds can be tested for their effect on Syk biological activity (e.g., kinase activity) using assays known in the art.

In general, candidate compounds are identified from large libraries of both natural product or synthetic (or semi-synthetic) extracts, chemical libraries, or from polypeptide or nucleic acid libraries, according to methods known in the art. Those skilled in the field of drug discovery and development will understand that the precise source of test extracts or compounds is not critical to the screening procedure(s) of the invention.

EXAMPLES

The present invention is illustrated by the following examples, which are in no way intended to be limiting of the invention.

Example 1. Syk Inhibitor Limits Intestinal and Lung Ischemia/Reperfusion (I/R) Injury Adult, 8-12 week old C57BL/6J mice were obtained (Jackson Lab, Boston, Mass.). Mice underwent at least a seven-day acclimatization prior to experimentation. All mice used in this study were maintained in specific pathogen-free conditions in the animal research facility at the Beth Israel Deaconess Medical Center (BIDMC).

Mice were randomly assigned to the following experimental groups: (a) mouse chow+sham procedures, (b) mouse chow+I/R procedures, (c) control chow+sham procedures, (d) control chow+I/R procedures, (e) R788 (3 g/kg)+sham procedures, (f) R788 (3 g/kg)+I/R procedures, and (g) R788 (5 g/kg)+I/R procedures (n=3 mice/group).

Syk inhibitor R788 was provided by Rigel Pharmaceuticals (South San Francisco, Calif.). Mice were fed food containing R788 (3 g/kg of chow, n=6 or 5 g/kg of chow, n=3), control chow (n=6), or regular chow (n=6). Food was prepared by Research Diets, Inc. (New Brunswick, N.J.). C57BL/6J mice were fed the R788-containing chow ad libitum for 6 days prior to experimentation in order to determine the effect of R788 on I/R injury.

Mice were anesthetized with 10 mg/kg of ketamine, 20 mg/kg of xylazine, and 3 mg/kg acepromazine intraperitoneally. In addition, 5 mg/kg ketamine and 3 mg/kg xylazine were given intramuscularly during the experiment when necessary. All procedures were performed on anesthetized spontaneously breathing animals while maintaining mouse body temperature at 37° C. using a controlled heating pad. All experiments were performed in accordance with the guidelines and approval of the Institutional Animal Care and Use Committee of the BIDMC.

Animals underwent I/R as had been described previously (Chiu et al., *Arch Surg.* 101: 478-483, 1970 and Fleming et al., *J Immunol.* 169: 2126-2133, 2002). Briefly, we performed a midline laparotomy before a 30-minute equilibration period. The superior mesenteric artery was identified and isolated. A small non-traumatic microvascular clip delivering approximately 85 grams of pressure was then applied for 30 minutes. The clip was removed after this ischemia phase, and the intestines were allowed to reperfuse for 3 hours. Sham-operated mice underwent the above-described surgical intervention without artery occlusion. The laparotomy incisions were sutured with 4.0 SOF-SILK™, the mice resuscitated with 1.0 mL pre-warmed sterile phosphate-buffered saline (PBS) subcutaneously, and monitored during the reperfusion period.

At the conclusion of the reperfusion period, mice were euthanized by carbon dioxide asphyxiation following the IAICUC Guidelines of the BIDMC. The small intestine was isolated and a 20-cm section distal to the gastroduodenal junction was removed and flushed with ice-cold PBS followed by ice-cold 10% phosphate-buffered formalin prior to overnight fixation in 10% phosphate-buffered foinialin. Lung removal consisted of intact extraction of the bronchial tree after expansion with 200-300 μL of 10% phosphate-buffered formalin and fixed overnight in 10% phosphate-buffered formalin. Formalin-fixed intestine and lung tissues were extensively washed in PBS, processed, and embedded in paraffin for histological, immunohistochemical (IHC), and immunofluorescence (IF) analysis, described below.

For histological analysis, 20-cm segments of small intestine specimens were fixed in 10% buffered formalin phosphate immediately after euthanasia. In the next step, tissues were embedded in paraffin, sectioned transversely in 5 μm sections, and stained with hematoxylin and eosin. For each section, we graded 50 villi on a six-tiered scale (Chiu et al., *Arch Surg.* 101: 478-483, 1970). To summarize, a normal villus was assigned a score of 0; villi with tip distortion were scored as 1; villi without goblet cells and with Guggenheims' spaces were scored as 2; villi with patchy disruption of the epithelial cells were scored as 3; villi with exposed but intact lamina propria and sloughing of epithelial cell were scored as 4; villi with exuding lamina propria were scored as 5; and villi with hemorrhage or denudation were scored as 6.

Alveolar and periluminal injury scores in each lung section were calculated based on Cooke's method (Cooke et al., *Blood* 8: 3230-3239, 1996). For each lung section, we examined 10-20 fields at high power field magnification (400×) and scored for alveolar infiltration on a 3-tiered scale. The calculation of alveolar scores was as follows: when no infiltrate was present, a score of 0 was given; when the infiltrate could be visualized easily only at 400×, a score of 1 was assigned; when infiltrates were readily visible, a score of 2 was assigned; and the score for consolidation was 3. Similarly, each section was scored for periluminal damage (airway or blood vessel) at 100×. The calculation for periluminal scores was as follows: when there was no infiltrate, a score of 0 was assigned; when the infiltrate was between 1-3 cell layers thick, a score of 1 was assigned; for infiltrates ranging from 4-10 cells layers thick, a score of 2 was assigned; and infiltrates >10 cell layers thick were scored as 3. Based on the overall involvement of the section, a severity score was calculated: the severity score for 0-25% involvement was 1; a severity score of 2 was assigned for 25-50% involvement; and the severity score for >50% involvement was 3. For calculation of the total lung injury score, the means of alveolar and periluminal scores for each section was totaled and multiplied by the severity score which gave a final score ranging from 0 to 18.

The data are presented as mean±standard error of the mean (SEM). The comparison of data was performed by one-way ANOVA with post hoc analysis using a Tukey test. When p<0.05, the differences were considered significant.

To determine the effect of Syk inhibition on mesenteric I/R injury, we first evaluated intestinal tissues. I/R groups had significantly more intestinal mucosal damage when compared to sham-operated mice groups. After 3 hours of reperfusion, the I/R groups exhibited significant mucosal injury (FIGS. 1A and 1B). The intestinal injury score in the mouse chow (MC)-I/R (2.7±0.53) and control chow (CC)-I/R (2.43±0.34) groups were significantly higher than MC-sham (0.44±0.06), CC-sham (0.32±0.04), and Syk inhibitor-sham (0.42±+0.33) (all p values≤0.001). Mice pre-treated with Syk inhibitor had significantly attenuated mucosal injury scores (3 g/kg R788: 0.58±0.08 vs. MC-I/R and CC-I/R, p values of 0.001 and 0.002, respectively; 5 g/kg R788: 0.92±0.14 vs. MC-I/R and CC-I/R, p values of 0.003 and 0.01, respectively). The injury scores in the Syk inhibitor-treated I/R mouse group were similar to those in the MC-sham group, the CC-sham group, and the Syk inhibitor-sham mice group (p values>0.05) (FIGS. 1A and 1B). We did not observe any differences in the preventive effect of Syk inhibitor at the 3 g/kg and 5 g/kg dosages.

Figure 2B:
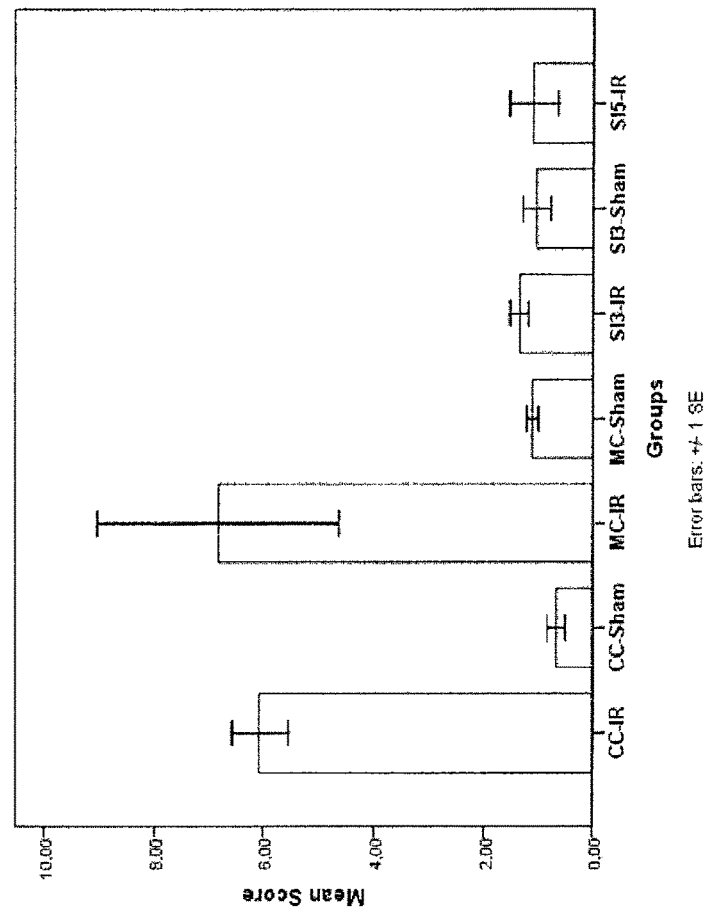

In order to evaluate whether Syk inhibitor could also prevent I/R-induced remote lung injury, we examined lung tissues. The average pulmonary damage score in the MC-I/R (6.83±2.2) mice was significantly higher than MC-sham (1.11±0.1), CC-sham (0.67±0.17), and Syk inhibitor-sham (1.03±0.26) groups (all p values<0.01). CC-I/R mice (6.07±0.52) group displayed more serious pulmonary injury than all of the sham groups (p values<0.05). Treatment with Syk inhibitor (3 g/kg R788: 1.36±0.18, 5 g/kg R788: 1.1±0.46) had reduced total lung injury scores when compared to MC-I/R and CC-I/R groups (p values<0.05). The injury scores in the Syk inhibitor-treated I/R mouse group were similar to those in MC-sham, CC-sham, and Syk inhibitor-sham mice groups (p values>0.05) (FIG. 2).

Thus, we have demonstrated that pre-treatment of mice with Syk inhibitor significantly reduces I/R injury in both intestinal and lung tissues.

Example 2. Immunohistochemistry and Immunofluorescence to Assess Intestine and Lung Syk and p-Syk Expression In order to perform immunohistochemistry (IHC) staining, formalin-fixed paraffin sections of intestine and lung were subjected to rehydration and antigen retrieval using a standard protocol. For IHC studies, the following reagents were used: rabbit anti-mouse Syk (N-19) (Santa Cruz, Calif.), rabbit anti-mouse p-Syk (phospho Y323) (Abeam, Inc.), and rabbit anti-mouse C3 (B-9) (Santa Cruz, Calif.).

For immunofluorescence (IF) staining, formalin-fixed paraffin-embedded sections were blocked with 10% BSA-PBS at room temperature for 1 hour and incubated with FITC-labeled primary or secondary antibodies at room temperature for 1 hour. The slides were washed, and coverslips were mounted with Dako Fluorescent mounting medium and analyzed by confocal microscopy (Nikon Eclipse Ti, Nikon Instruments, Melville, N.Y.). FITC-labeled goat anti-mouse IgG (Santa Cruz, Calif., sc2010), FITC-labeled rat anti-mouse C3 (11H9) (Santa Cruz, Calif., sc-58926), FITC-labeled goat anti-mouse IgM (Southern Biotech, 1021-02), and FITC-labeled rat anti-mouse Ly-6G and LY-6C (Clone R6B-8C5) (BD Pharmingen) were the antibodies used in these studies.

Syk expression in the intestine and lung were evaluated by IHC. Syk staining in intestines and lungs were more prominent in I/R groups than in sham-operated groups. However, pre-treatment with Syk inhibitor did not cause any changes in Syk staining in either the intestine or the lung (FIGS. 3A and 3B).

Because the Syk inhibitor suppresses the expression of phosphorylated Syk (p-Syk), the active form of Syk, we performed p-Syk staining by using IHC and IF. We observed staining in I/R group mice. There was no staining in sham-operated mice groups. In the I/R mice group, Syk inhibitor treatment eliminated p-Syk staining in the lung and intestine (FIGS. 3C and 3D). There was only faint staining with p-Syk in the lung and intestine. After a 3-hour reperfusion, we detected only slight p-Syk staining. These results suggest that Syk phosphorylation is an early event in I/R-induced damage.

Example 3. Deposition of IgM, IgG, and C3 in Intestine and Lung Samples

Reperfusion after ischemia induced alteration of the endothelial membrane and allows neoantigen expression. Circulating natural IgM antibodies bind to these antigens and may trigger complement-mediated injury (Williams et al., *J Applied Physiol.* 86: 938-942, 1999). Therefore, we performed IgM staining by IF, as described above. There was increased IgM staining in I/R intestinal and lung samples when compared to the sham tissues. In addition, we observed that Syk inhibitor reduced IgM deposition and, hence, detection by immunofluorescence staining in both tissues (FIGS. 4A and 4B). Unlike the differences detected for natural IgM staining, we were only able to detect minimal IgG staining in all groups (data not shown).

It has been reported that I/R activates the complement system, as indicated by C3 deposition on the intestine (Williams et al., supra). To determine whether Syk inhibitor prevents complement deposition, we performed IHC (FIGS. 5A and 5B) and IF (FIGS. 5C and 5D) staining. When compared to the staining in sham-operated groups, mice subjected to I/R had prominent deposition of complement component 3 protein (C3) on the surface of epithelial cells. Treatment of mice with Syk inhibitor attenuated C3 staining in the intestinal mucosa. Similar to our observation in the intestine, there was significant deposition of C3 in the lungs of mice subjected to I/R when compared to animals subjected to the sham operation. Mice treated with Syk inhibitor displayed limited C3 deposition in the lungs.

It was suggested that infiltration by neutrophils mediates local tissue damage in response to I/R (Conner et al., *J Surg Res.* 84: 24-30, 1999). Therefore, we evaluated the presence of neutrophils in the intestine and lung after sham and I/R procedures in mice treated with Syk inhibitor. Mice subjected to I/R had more prominent GR-1 staining within the intestinal tissue after 3-hour reperfusion when compared to the sham-operated mice group. The administration of Syk inhibitor to mice prevented I/R-induced neutrophil infiltration. In addition, Syk inhibitor treatment decreased infiltration in the lung tissues (FIGS. 6A and 6B).

Example 4. Inhibition of Syk Expression with Syk-Specific siRNA

Figure 7A:
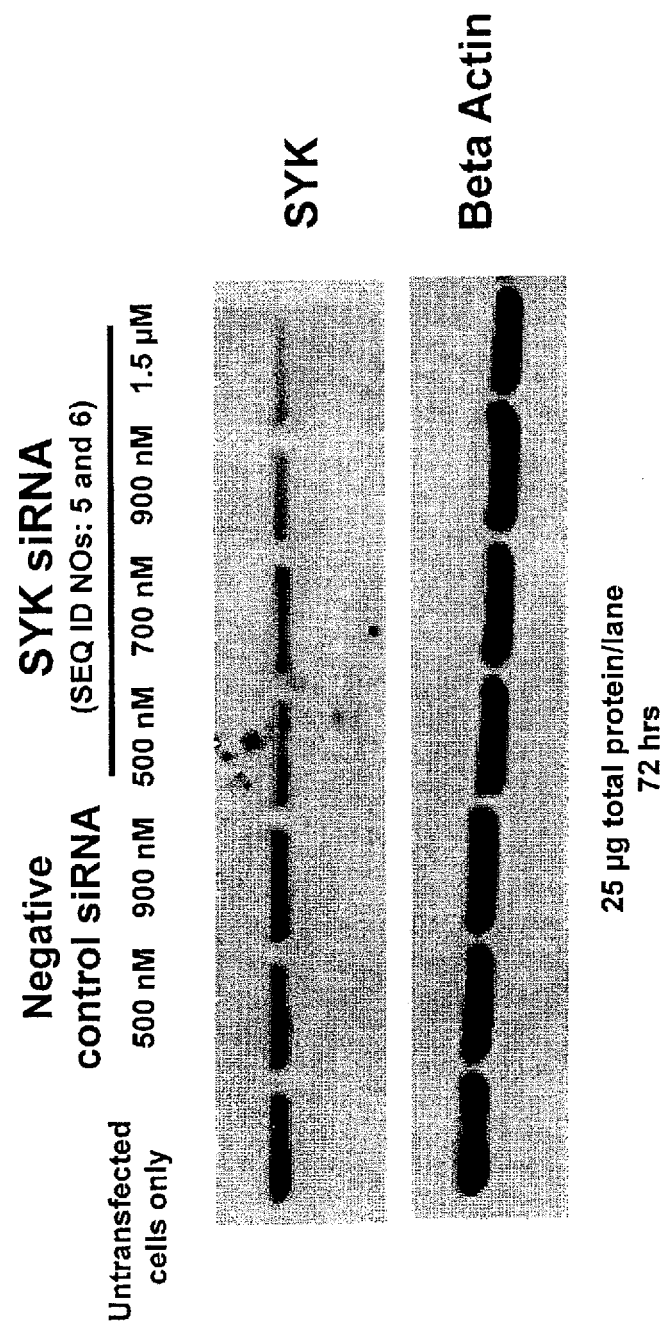
FIGS. 7A-7C show that Syk expression can be inhibited with Syk-specific siRNA.
Figure 7B:
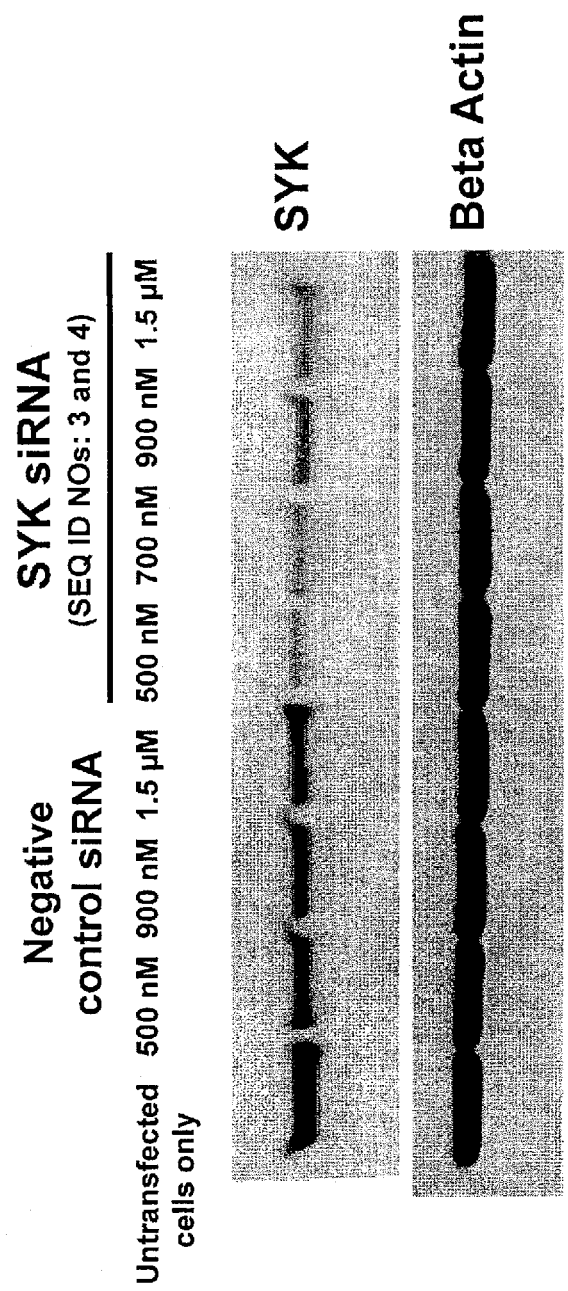
Figure 7C:
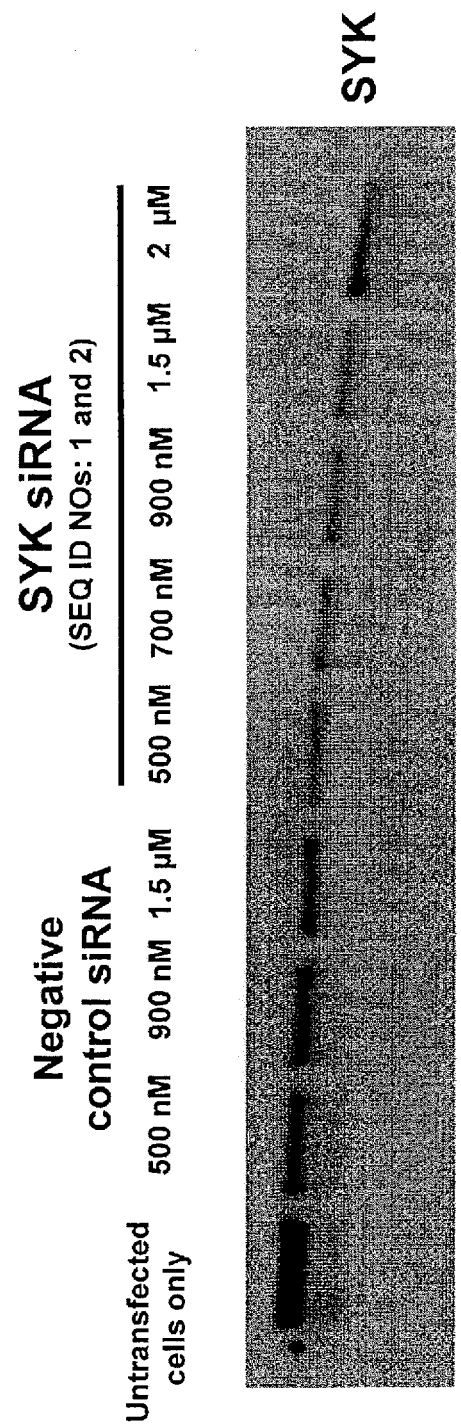

Different concentrations (0.5, 0.7, 0.9, 1.5, and 2 μM per million) of T cells were transfected by electroporation using Amexa Nucleofector solution. Briefly, a total of $5 \times 10^6$ T cells were re-suspended in 100 μl Nucleofector solution (Lonza Walkerrsville Inc.; Walkersville, Md.). The desired amount of Syk siRNA was mixed in with the T cell/nucleofector suspension and electrporated. The transfected cells were plated in RPMI-1640 medium without any antibiotic and incubated for approximately 72 hours. After proper incubation, transfected T cells were lysed in RIPA buffer, and Western blotting was performed with an antibody against total Syk (Clone 4D10; Santa Cruz Biotechnology, Inc.; Santa Cruz, Calif.). FIGS. 7A-7C show that Syk expression is inhibited when cells are transfected with Syk-specific siRNA corresponding to SEQ ID NOs: 1-6.

Other Embodiments

From the foregoing description, it is apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

The invention claimed is:

1. A method of treating or reducing the likelihood of an ischemia-reperfusion injury in a subject, said method comprising providing to said subject R406, or a pharmaceutically acceptable salt thereof, or fostamatinib, or a pharmaceutically acceptable salt thereof, in an amount and for a duration that together are sufficient to treat or reduce the likelihood of said ischemia-reperfusion injury in said subject, wherein said ischemia-reperfusion injury is the result of an inflammatory disorder, myocardial infarction, atherosclerosis, peripheral vascular disorder, a pulmonary embolus, a venous thrombosis, a transient ischemic attack, unstable angina, cerebral vascular ischemia, stroke, an ischemic neurological disorder, ischemic kidney disease, vasculitis, transplantation, endarterectomy, aneurysm repair surgery, or traumatic injury.

2. A method of attenuating ischemia-reperfusion injury in a subject in need thereof, said method comprising providing to said subject R406, or a pharmaceutically acceptable salt thereof, or fostamatinib, or a pharmaceutically acceptable salt thereof, in an amount and for a duration that together are sufficient to attenuate said ischemia-reperfusion injury in said subject, wherein said ischemia-reperfusion injury is the result of an inflammatory disorder, myocardial infarction, atherosclerosis, peripheral vascular disorder, a pulmonary embolus, a venous thrombosis, a transient ischemic attack, unstable angina, cerebral vascular ischemia, stroke, an ischemic neurological disorder, ischemic kidney disease, vasculitis, transplantation, endarterectomy, aneurysm repair surgery, or traumatic injury.

3. The method of claim 1, wherein said R406, or pharmaceutically acceptable salt thereof, or fostamatinib, or pharmaceutically acceptable salt thereof, is provided prior to the onset of said ischemia-reperfusion injury.

4. The method of claim 1, wherein said R406,or pharmaceutically acceptable salt thereof, or fostamatinib, or pharmaceutically acceptable salt thereof, is provided concurrently with the onset of said ischemia-reperfusion injury.

5. The method of claim 1, wherein said R406, or pharmaceutically acceptable salt thereof, or fostamatinib, or pharmaceutically acceptable salt thereof, is provided after the onset of said ischemic-reperfusion injury.

6. The method of claim 1, wherein said R406, or a pharmaceutically acceptable salt thereof, or fostamatinib, or pharmaceutically acceptable salt thereof, is provided orally, intravenously, or parenterally.

7. The method of claim 1, wherein said R406, or pharmaceutically acceptable salt thereof, or fostamatinib, or pharmaceutically acceptable salt thereof, reduces or inhibits the biological activity or expression level of a Syk protein.

8. The method of claim 1, wherein said method further comprises providing an additional therapeutic agent to said subject.

9. The method of claim 8, wherein said additional therapeutic agent is an anti-inflammatory agent, a vasodilator, a beta blocker, a statin, a calcium channel blocker, an angiotensin-converting enzyme inhibitor, ranolazine, or an anticoagulant.

10. The method of claim 1, wherein said subject is human.

11. The method of claim 1, wherein the method comprises providing R406, or a pharmaceutically acceptable salt thereof, to the subject.

12. The method of claim 1, wherein the method comprises providing fostamatinib, or a pharmaceutically acceptable salt thereof, to the subject.

13. The method of claim 2, wherein the method comprises providing R406, or a pharmaceutically acceptable salt thereof, to the subject.

14. The method of claim 2, wherein the method comprises providing fostamatinib, or a pharmaceutically acceptable salt thereof, to the subject.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
ggauaagaac aucauagaat t                                             21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
uucuaugaug uucuuaucct t                                             21

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
cgcucuuaaa gaugaguuat t                                             21

<210> SEQ ID NO 4
<211> LENGTH: 21
<212> TYPE: RNA
<213> ORGANISM: Artificial Sequence
<220> FEATURE:
<223> OTHER INFORMATION: Synthetic Construct

<400> SEQUENCE: 4
uaacucaucu uuaagagcgg g                                             21

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
gcacuaucgc aucgacaaat t                                             21
```

```
<210> SEQ ID NO 6
<211> LENGTH: 21
<212> TYPE: RNA
<213> ORGANISM: Artificial Sequence
<220> FEATURE:
<223> OTHER INFORMATION: Synthetic Construct

<400> SEQUENCE: 6
uuugucgaug cgauagugca g                                      21
```